United States Patent [19]

Lavielle et al.

[11] Patent Number: 5,387,591
[45] Date of Patent: Feb. 7, 1995

[54] PYRROLIDINE COMPOUNDS

[75] Inventors: Gilbert Lavielle, La Celle Saint Cloud; Thierry Dubuffet, L'Hay les Roses; Olivier Muller, Emmery; Michel Laubie, Vaucresson; Tony Verbeuren, Vernouillet, all of France

[73] Assignee: Adir et Compagnie, Courbevoie, France

[21] Appl. No.: 16,501

[22] Filed: Feb. 11, 1993

[30] Foreign Application Priority Data

Feb. 12, 1992 [FR] France .................. 92 01523

[51] Int. Cl.⁶ ............................. A61K 31/47
[52] U.S. Cl. ....................... 514/307; 514/311; 514/542; 546/147; 546/172; 548/542
[58] Field of Search ........... 548/542; 514/424, 307, 514/311; 546/147, 172

[56] References Cited

PUBLICATIONS

Tetrahedron Letters, vol. 29, No. 23 pp. 2797–2800 1988, Becking et al.

Primary Examiner—José G. Dees
Assistant Examiner—Samuel Barts
Attorney, Agent, or Firm—Gordon W. Hueschen

[57] ABSTRACT

Compounds of formula (I):

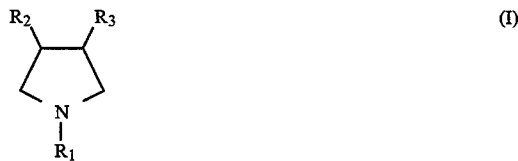

in which:

$R_1$ represents:
  optionally substituted alkyl,
  optionally substituted phenyl,
  pyridyl,
  optionally substituted phenylsulfonyl,
  acyl,
  optionally substituted benzoyl or pyridylcarbonyl,
  alkylaminocarbonyl or phenylaminocarbonyl,
  acylamino or benzoylamino, $R_2$ represents:
  hydrogen,
  optionally substituted phenyl,
  optionally substituted 3-pyridyl or 2-pyridyl, $R_3$ represents any one of the following groups:

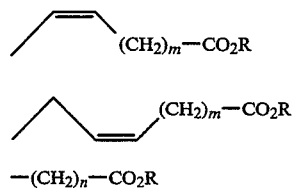

$-(CH_2)_n-CO_2R$ in which
  m is equal to 2, 3 or 4,
  n is equal to 4, 5, 6 or 7, and R represents hydrogen or alkyl.

8 Claims, No Drawings

PYRROLIDINE COMPOUNDS

The present invention relates to new pyrrolidine compounds. More particularly, the compounds described in the present invention possess antithromboxane $A_2$ properties both as antagonists of thromoboxane $A_2$ (TXA$_2$) receptors and as inhibitors of the activity of the enzyme responsible for the synthesis of thromboxane $A_2$: thromboxane $A_2$-synthase. Thromboxane $A_2$ is a metabolite of arachidonic acid which is produced by blood platelets and which causes substantial constriction of the blood vessels and induces aggregation of the platelets. The production of thromboxane $A_2$ is increased in diseases such as angina pectoris or cerebrovascular accident and it plays a very important role in all processes leading to thrombotic diseases.

It was therefore particularly advantageous to synthesize substances capable of inhibiting the proaggregation and vasoconstrictive activities of thromboxane $A_2$ either as antagonists of thromboxane $A_2$ receptors or as inhibitors of thromboxane $A_2$-synthase.

Pyrrolidine compounds possessing antithrombotic properties have been described in the literature. This is the case, in particular, for the compounds described in Patents EP 289 911 and EP 367 130.

The compounds described in the present invention, in addition to the fact that they are new, possess pharmacological properties which are substantially more potent than those of other compounds described in the prior art.

They are therefore useful as antagonists of thromboxane $A_2$ and as inhibitors of thromboxane $A_2$-synthase in the treatment or prevention of thrombotic diseases such as cerebrovascular accident, angina pectoris, myocardial infarction, peripheral circulatory insufficiency, diseases associated with the formation of thrombus and the like.

More specifically, the present invention relates to the compounds of formula (I):

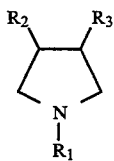

(I)

in which:

$R_1$ represents:

linear or branched (C$_1$-C$_6$)alkyl which is unsubstituted or substituted by 2-pyridyl, 3-pyridyl or phenyl (which is itself optionally substituted by one or more halogen or linear or branched (C$_1$-C$_6$)alkyl, linear or branched (C$_1$-C$_6$)alkoxy or trihalomethyl), phenyl which is unsubstituted or substituted by one or more halogen or linear or branched (C$_1$-C$_6$)alkyl, linear or branched (C$_1$-C$_6$)alkoxy or trihalomethyl, pyridyl, phenylsulfonyl (which is unsubstituted or substituted on the phenyl ring by one or more halogen or linear or branched (C$_1$-C$_6$)alkyl, linear or branched (C$_1$-C$_6$)alkoxy or trihalomethyl), naphthylsulfonyl, quinolylsulfonyl group or isoquinolylsulfonyl, linear or branched (C$_1$-C$_6$)acyl, benzoyl or pyridylcarbonyl which is unsubstituted or substituted on the aromatic ring by one or more halogen or linear or branched (C$_1$-C$_6$)alkyl, linear or branched (C$_1$-C$_6$)-alkoxy or trihalomethyl, alkylaminocarbonyl or phenylaminocarbonyl, acylamino or benzoylamino, $R_2$ represents:

hydrogen, phenyl which is unsubstituted or substituted by one or more halogen or linear or branched (C$_1$-C$_6$)alkyl, linear or branched (C$_1$-C$_6$)alkoxy, hydroxyl or trihalomethyl, 3-pyridyl or 2-pyridyl which is unsubstituted or substituted on the pyridine ring by one or more halogen or linear or branched (C$_1$-C$_6$)alkyl, linear or branched (C$_1$-C$_6$)alkoxy, or trihalomethyl, $R_3$ represents any one of the following groups:

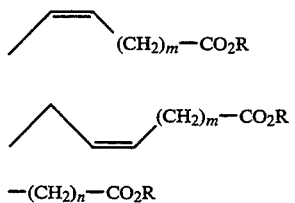

$-(CH_2)_n-CO_2R$ in which m is equal to 2, 3 or 4, n is equal to 4, 5, 6 or 7, and R represents hydrogen or a linear or branched (C$_1$-C$_6$)alkyl, their enantiomers, diastereoisomers and epimers as well as their addition salts with a pharmaceutically acceptable acid or base.

Among the pharmaceutically acceptable acids, hydrochloric, sulfuric, tartaric, maleic, fumaric, methanesulfonic, and camphoric acids and the like may be mentioned with no limitation being implied.

Among the pharmaceutically acceptable bases, sodium hydroxide, potassium hydroxide, tert-butylamine, diethylamine and ethylenediamine may be mentioned with no limitation being implied.

The invention also extends to the process for preparing the compounds of formula (I), wherein there is used as starting material a pyrrolidine of formula (II):

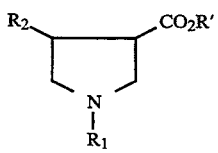

(II)

in which $R_1$ and $R_2$ have the same meaning as in formula (I) and R' represents a linear or branched (C$_1$-C$_6$)alkyl group, which compound of formula (II), in racemic or isomeric form, when it is in the form of a pair of enantiomers, may be converted to its other pair of enantiomers by epimerization in a sodium alcoholate, which is reacted:

1 either with lithium aluminum hydride in an inert solvent, to give the pyrrolidine of formula (III)

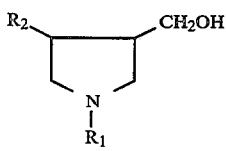 (III)

in which $R_1$ and $R_2$ have the same meaning as in formula (I), which is reacted:
either with gaseous hydrochloric acid in the presence of thionyl chloride in chloroformic medium, to give the pyrrolidine of formula (IV):

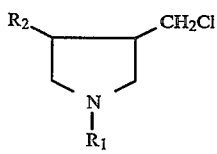 (IV)

in which $R_1$ and $R_2$ have the same meaning as in formula (I), which is converted to pyrrolidine of formula (V) in the presence of tert-butylammonium cyanide, in dimethylformamide:

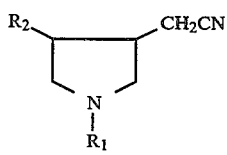 (V)

in which $R_1$ and $R_2$ have the same meaning as in formula (I),
or with para-toluenesulfonyl chloride in pyridine to give the pyrrolidine of formula (VI):

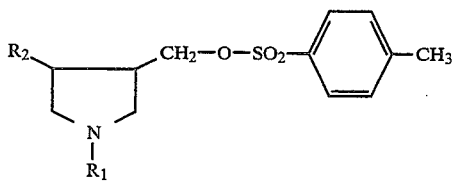 (VI)

in which $R_1$ and $R_2$ have the same meaning as in formula (I), which is converted to the above-described pyrrolidine of formula (V), in the presence of potassium cyanide in dimethyl sulfoxide, which compound of formula (V) is reduced by means of diisobutylaluminum hydride, to give the aldehyde of formula (VII):

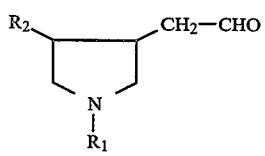 (VII)

in which $R_1$ and $R_2$ have the same meaning as in formula (I),
2 or with diisobutylaluminum hydride, to give the aldehyde of formula (VIII):

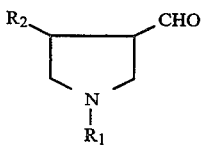 (VIII)

in which $R_1$ and $R_2$ have the same meaning as in formula (I), which is, if desired, reacted with the phosphorus ylide of formula (IX), prepared by reaction of the corresponding phosphonium salt in the presence of potassium tert-butanolate in tetrahydrofuran, $(C_6H_5)_3 P=CHOCH_3$ (IX)

to give the compound of formula (X)

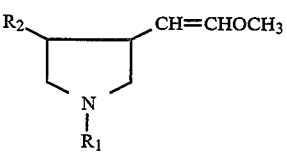 (X)

in which $R_1$ and $R_2$ have the same meaning as in formula (I), which is treated with trifluoroacetic acid to give the above-described aldehyde of formula (VII), which compounds of formula (VII) or (VIII) are reacted with a phosphorus ylide of formula (XI), prepared by reaction of the corresponding phosphonium salt in the presence of potassium tert-butanolate in tetrahydrofuran, $(C_6H_5)_3 P=CH-(CH_2)_m-CO_2H$ (XI)

in which m has the same meaning as in formula (I), to give the compounds of formula (I/a) or (I/b) respectively, which are specific examples of the compounds of formula (I):

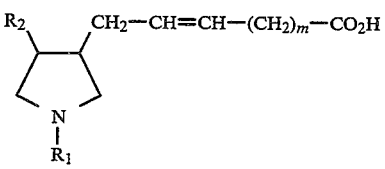 (I/a)

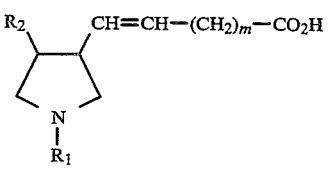 (I/b)

in which compounds $R_1$, $R_2$ and m have the same meaning as in formula (I), which compounds of formula (I/a) or (I/b)
are esterified, if desired, to give the corresponding compounds of formula (I/a₁) and (I/b₁):

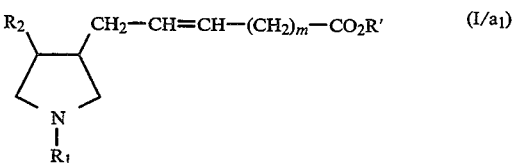 (I/a₁)

-continued

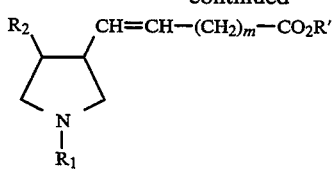
(I/b₁)

in which compounds $R_1$ and $R_2$ have the same meaning as in formula (I) and R' represents a linear or branched ($C_1$-$C_6$)alkyl group, whose double bond is optionally reduced by catalytic hydrogenation to give the compound of formula (I/c), which is a specific example of the compounds of formula (I),

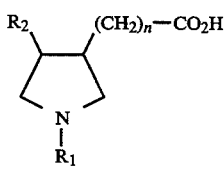
(I/c)

in which $R_1$, $R_2$ and n have the same meaning as in formula (I), and which is converted, if desired, to the corresponding ester of formula (I/c₁):

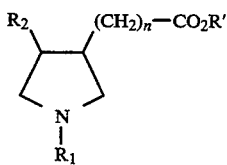
(I/c₁)

in which $R_1$ and $R_2$ have the same meaning as in formula (I) and R' represents a linear or branched ($C_1$-$C_6$)alkyl group, which compounds of formula (I/a), (I/a₁), (I/b), (I/b₁), (I/c), (I/c₁) constitute the set of compounds of formula (I), which compounds, when $R_2$ represents a phenyl ring substituted by a linear or branched ($C_1$-$C_6$)alkoxy group, can be converted, if desired, to compounds of formula (I) in which $R_2$ represents a phenyl ring substituted by a hydroxyl group, which are purified, where appropriate, using a conventional purification technique, whose isomers are optionally separated using a conventional purification technique, and which are converted, if desired, to their addition salts with a pharmaceutically acceptable acid or base.

Furthermore, the compounds corresponding more specifically to the formula (I'), which is a specific example of the compounds of formula (I):

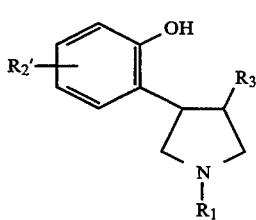
(I')

in which $R_1$ and $R_3$ have the same meaning as in formula (I), $R'_2$ represents a hydrogen atom, a halogen atom or a linear or branched ($C_1$-$C_6$)alkyl, linear or branched ($C_1$-$C_6$)alkoxy or trihalomethyl group, are also obtained using the process wherein there is used as starting material the compound of formula (XII):

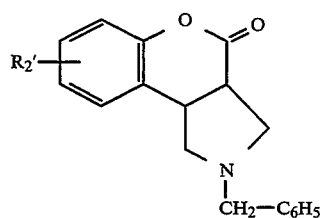
(XII)

in which $R'_2$ has the same meaning as in formula (I'), which is reduced by means of diisobutylaluminum hydride, to give the compound of formula (XIII):

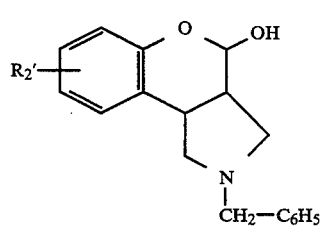
(XIII)

in which $R'_2$ has the same meaning as above, which is:

a either:

either converted to the compound of formula (XIV), by catalytic hydrogenation (Pd/c) in dioxane:

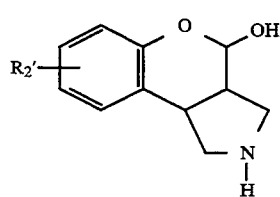
(XIV)

which is treated with a halogenated derivative of formula $R_1X$ in which $R_1$ has the same meaning as in formula (I) and X represents a halogen atom, in chloroform in the presence of triethylamine, to give the compound of formula (XV):

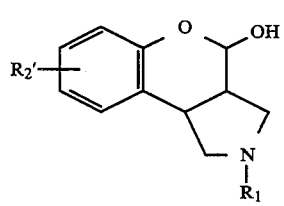
(XV)

in which $R'_2$ and $R_1$ have the same meaning as above, or converted to the compound of formula (XVI), by catalytic hydrogenation (Pd/c) in a hydrochloric acid/ethanol medium:

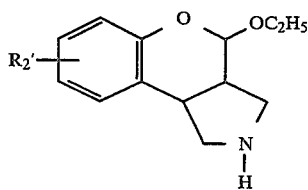 (XVI)

in which R'₂ has the same meaning as above, which is treated with a halogenated derivative of formula R₁X, described above, to give the compound of formula (XVII):

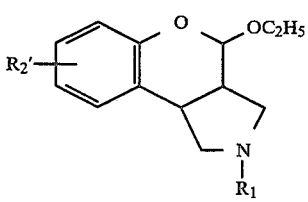 (XVII)

in which R'₂ and R₁ have the same meaning as above, which is treated with trifluoroacetic acid, to give the above- described compound of formula (XV), which compound of formula (XV) is then reacted with the phosphorus ylide of formula (IX) prepared by reaction of the corresponding phosphonium salt, in the presence of potassium tert-butanolate in tetrahydrofuran, $(C_6H_5)_3 P=CHOCH_3$ (IX)

to give the compound of formula (XVIII):

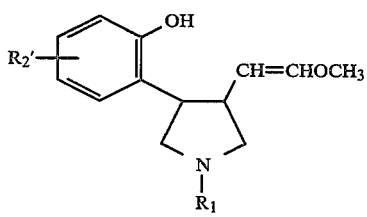 (XVIII)

in which R₁ and R'₂ have the same meaning as above, whose diastereoisomers are optionally separated using a conventional separation technique, which compound is treated with trifluoroacetic acid to give the aldehyde of formula (XIX):

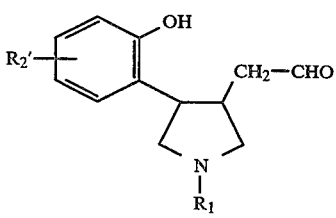 (XIX)

in which R₁ and R'₂ have the same meaning as above, whose diastereoisomers are optionally separated using a conventional separation technique, b or reacted with the above-described phosphorus ylide of formula (IX), to give a compound of formula (XX):

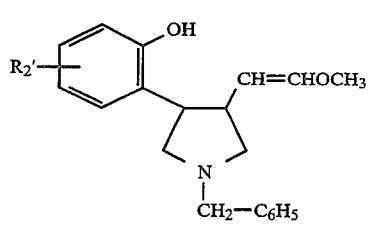 (XX)

in which R'₂ has the same meaning as above, whose diastereoisomers are optionally separated using a conventional separation technique, which compound is treated with trifluoroacetic acid, to give the aldehyde of formula (XIX/a), which is a specific example of the compounds of formula (XIX):

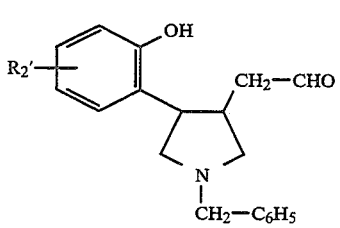 (XIX/a)

in which R'₂ has the same meaning as above, whose diastereoisomers are optionally separated using a conventional separation technique, which compounds of formula (XIII) or (XIX) are reacted with a phosphorus ylide of formula (X), prepared by reaction of the corresponding phosphonium salt in the presence of potassium tert-butanolate in tetrahydrofuran, $(C_6H_5)_3 P=CH-(CH_2)_m-CO_2H$ (X)

in which m has the same meaning as in formula (I), to give the compounds of formulae (I/d) and (I/e) respectively, which are specific examples of the compounds of formula (I):

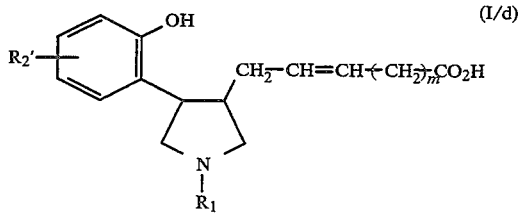 (I/d)

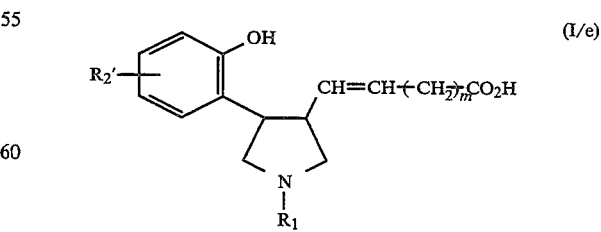 (I/e)

in which compounds R₁ and R'₂ have the same meaning as above, which are esterified, if desired, to give the corresponding compounds of formulae (I/d₁) and (I/e₁):

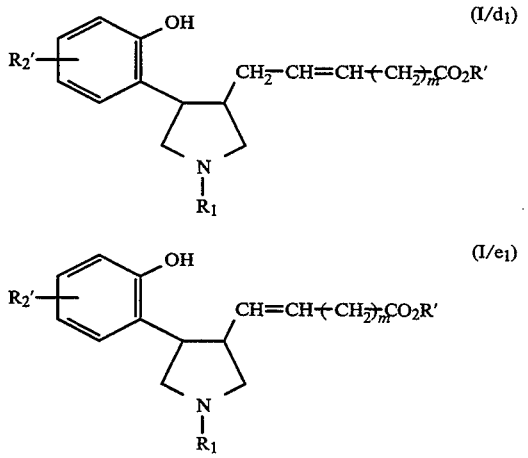

in which compounds $R_1$ and $R'_2$ have the same meaning as above and $R'$ represents a linear or branched ($C_1$-$C_6$)alkyl group,
whose double bond is optionally reduced by catalytic hydrogenation to give the compound of formula (I/f), which is a specific example of the compounds of formula (I):

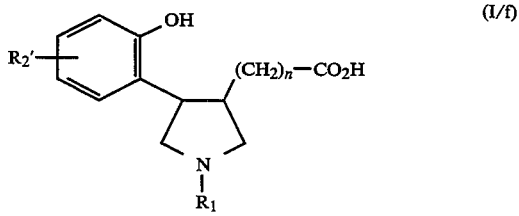

in which $R_1$ and $R'_2$ have the same meaning as above, and which is converted, if desired, to the corresponding ester of formula (I/f$_1$):

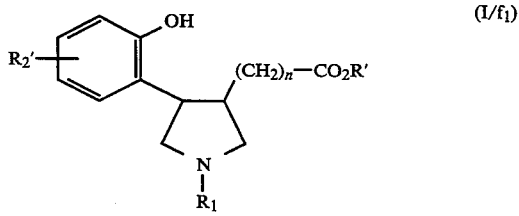

in which $R_1$, $R'_2$ and $R'$ have the same meaning as above, which compounds of formula (I/d), (I/d$_1$), (I/e), (I/e$_1$), (I/f) and (I/f$_1$) constitute the set of compounds of formula (I'),
which compounds, when $R'_2$ represents a linear or branched ($C_1$-$C_6$)alkoxy group, may be converted, if desired, to compounds of formula (I') in which $R'_2$ represents a hydroxyl group,
which are purified, where appropriate, using a conventional purification technique,
whose isomers are optionally separated using a conventional purification technique,
and which are converted, if desired, to their addition salts with a pharmaceutically acceptable acid or base.

The compounds of formula (II), which are used as starting materials, are prepared according to the process described in J. Chem. Soc., Chem. Comm., 1566, 1985, or according to the process described in Chem. Pharm. Bull, 33, 2762, 1985 and Organic Synthesis, 67, 133, 1988.

The compounds of formula (XII), which are used as starting material, are prepared using the process described in Chem. Pharm. Bull, 33, 2762, 1985 and Organic Synthesis, 67, 133, 1988.

The compounds of formula (I) possess very advantageous pharmacological properties. In particular, they are capable of inhibiting platelet aggregation induced by U46619 (9,11-dideoxy-11α,9α-epoxymethanoprostaglandin F$_2$α), an agonist of TXA$_2$ receptors, of inhibiting contractions caused by U46619 in guinea pig trachea and of preventing in vivo bronchoconstrictions induced by U46619 in guinea pigs. Furthermore, the compounds inhibit the synthesis of TXA$_2$ in rabbit blood.

The subject of the present invention is also the pharmaceutical compositions containing as active ingredient at least one compound of formula (I) alone or in combination with one or more nontoxic inert excipients or vehicles.

Among the pharmaceutical compositions according to the invention, there may be mentioned more particularly those which are suitable for oral, parenteral or nasal administration, simple or sugared tablets, sublingual tablets, hard gelatine capsules, lozenges, suppositories, creams, ointments, skin gels and the like.

The effective dosage will vary according to the age and weight of the patient, the nature and severity of the infection as well as the route of administration. The latter may be oral, nasal, rectal or parenteral. Generally, the unit dosage ranges between 10 and 200 mg for a treatment using 1 to 3 doses per 24 hours. The following examples illustrate the invention and do not limit it in any manner.

The starting materials used are products which are known or which are prepared according to known procedures. The letters α and β mean that the hydrogen atoms in pyrrolidine are in cis relative to each other in the case of (3α, 4α) and in trans relative to each other in the case of (3α, 4β).

EXAMPLE 1:
(4Z)-5-[(3α,4β)-1-METHYL-4-(2-METHOXYPHENYL) PYRROLIDIN-3-YL]PENT-4-ENOIC ACID, SODIUM SALT

Stage A:
[(3α,4β)-1-Methyl-4-(2-methoxyphenyl)pyrrolidin-3-yl]formaldehyde

To 20.8 mmol of methyl [(3α,4β)-1-methyl-4-(2-methoxyphenyl) pyrrolidin-3-yl]carboxylate (prepared according to the process described in J. Chem. Soc., Chem. Comm., 1566, 1985) in 160 ml of toluene and 40 ml of pentane, are added at −78° C., 41.6 ml of a 1M solution of diisobutylaluminum hydride in hexane. The reaction medium is stirred for one hour at −78° C. and then treated with a methanol/water mixture (1/1). After evaporation, the salts are filtered and washed with acetonitrile. The filtrates are then evaporated. The expected product is obtained after purification on a silica column using as elution solvent a dichloromethane/methanol mixture (90/10).
Yield: 61%

| Elemental microanalysis: | | | |
|---|---|---|---|
| | C % | H % | N % |
| Calculated | 71.21 | 7.81 | 6.39 |
| Found | 70.94 | 7.60 | 6.22 |

Proton Nuclear Magnetic Resonance (CDCl$_3$/TMS)

The coupling constant J for the two geminate protons 3α and 4β in pyrrolidine is equal to 7.4 Hz.

Stage B:
(4Z)-5-[(3α,4β)-1-Methyl-4-(2-methoxyphenyl) pyrrolidin-3-yl]pent-4-enoic acid, sodium salt To 5.5 mmol of (3-carboxypropyl)triphenylphosphonium bromide in 15 ml of tetrahydrofuran are slowly added, at room temperature, 11 ml of a 1M solution of potassium tert-butoxide in tetrahydrofuran. The reaction medium is stirred for 1 hour. 5.5 mmol of the compound obtained in the preceding stage, in solution in 30 ml of THF, are then added and the mixture is stirred for 2 hours. The reaction medium is then treated with a saturated solution of ammonium chloride. After evaporation, a 1N aqueous solution of sodium hydroxide is added to the residue. This aqueous phase is washed with ether and acidified by means of 1N hydrochloric acid. After extraction with dichloromethane, drying and evaporation, the expected product is purified by chromatography on a silica column, using as elution solvent a dichloromethane/methanol mixture (95/5). The acid is then converted to the corresponding sodium salt.

| Elemental microanalysis: | | | |
|---|---|---|---|
| | C % | H % | N % |
| Calculated | 65.58 | 7.12 | 4.50 |
| Found | 65.27 | 6.77 | 4.50 |

Examples 2 to 5 were obtained using the same procedure as that described for Example 1, using the appropriate starting materials.

EXAMPLE 2: (4Z)-5-[(3α,4β)-1-METHYL-4-(4-FLUOROPHENYL) PYRROLIDIN-3-YL]PENT-4-ENOIC ACID, SODIUM SALT

| Elemental microanalysis: | | | |
|---|---|---|---|
| | C % | H % | N % |
| Calculated | 64.20 | 6.40 | 4.68 |
| Found | 64.29 | 6.16 | 4.52 |

EXAMPLE 3: (4Z)-5-[(3α,4β)-1-METHYL-4-(PHENYL)PYRROLIDIN-3-YL]PENT-4-ENOIC ACID, SODIUM SALT

| Elemental microanalysis: | | | |
|---|---|---|---|
| | C % | H % | N % |
| Calculated | 68.31 | 7.17 | 4.98 |
| Found | 68.02 | 6.84 | 5.09 |

EXAMPLE 4: (5Z)-6-[(3α,4β)-1-METHYL-4-(4-FLUOROPHENYL) PYRROLIDIN-3-YL]HEX-5-ENOIC ACID, SODIUM SALT

| Elemental microanalysis: | | | |
|---|---|---|---|
| | C % | H % | N % |
| Calculated | 65.16 | 6.76 | 4.47 |
| Found | 65.29 | 6.90 | 4.09 |

EXAMPLE 5: (5Z)-6-[(3α,4β)-1-METHYL-4-(PHENYL)PYRROLIDIN-3-YL]HEX-5-ENOIC ACID, SODIUM SALT

| Elemental microanalysis: | | | |
|---|---|---|---|
| | C % | H % | N % |
| Calculated | 69.13 | 7.51 | 4.74 |
| Found | 68.74 | 7.10 | 4.97 |

EXAMPLE 6: (5Z)-7-[(3α,4β)-1-METHYL-4-(4-FLUOROPHENYL) PYRROLIDIN-3-YL]HEPT-5-ENOIC ACID, SODIUM SALT

Stage A: (3α,4β) -1-Methyl-3-hydroxymethyl-4-(4-fluorophenyl)pyrrolidine

To a suspension containing 300 mmol of lithium aluminum hydride in 800 ml of tetrahydrofuran and 200 ml of ethyl ether are added, at 10° C., 200 mmol of ethyl [(3α,4α)-1-methyl-4-(4-fluorophenyl)pyrrolidin-3-yl]carboxylate (prepared according to the procedure described in J. Chem. Soc., Chem. Comm., 1566, 1985) in 100 ml of THF. The mixture is kept at 10° C. for 30 minutes and then treated successively with 100 ml of ethyl acetate and then 1 liter of water.

After extraction with ether, drying and evaporation, the expected product is purified by chromatography on a silica column, using as eluent a dichloromethane/methanol mixture (80/20).

Yield: 90%

| Elemental microanalysis: | | | |
|---|---|---|---|
| | C % | H % | N % |
| Calculated | 68.87 | 7.70 | 6.99 |
| Found | 68.61 | 7.63 | 6.56 |

Proton Nuclear Magnetic Resonance (CDCl$_3$/TMS)

The coupling constant J for the two geminate protons 3α and 4α in pyrrolidine is equal to 7.5 Hz.

Stage B:
(3α,4α)-1-Methyl-3-chloromethyl-4-(4-fluorophenyl) pyrrolidine

A solution containing 95 mmol of the product obtained in the preceding stage, in 300 ml of chloroform, is saturated with gaseous hydrochloric acid and refluxed for 30 minutes. After cooling to 30° C., a solution containing 191 mmol of thionyl chloride in 90 ml of chloroform is slowly added. The mixture is refluxed for 3 hours. The solvent is then evaporated and the product crystallized in hydrochloride form and is displaced from its salt with sodium hydroxide and extracted with dichloromethane.

Yield: 95% as hydrochloride

| Elemental microanalysis (hydrochloride): | | | | |
|---|---|---|---|---|
| | C % | H % | N % | Cl % |
| Calculated | 54.56 | 6.10 | 5.30 | 26.84 |
| Found | 54.34 | 5.91 | 5.27 | 26.60 |

Stage C:
(3α,4α)-1-Methyl-3-cyanomethyl-4-(4-fluorophenyl)pyrrolidine

To 85 mmol of the product obtained in the preceding stage, in 400 ml of dimethylformamide, are added 153 mmol of tetrabutylammonium cyanide. The mixture is heated for 8 hours at 75° C. and then hydrolyzed. After extraction with dichloromethane, the expected product is obtained after purification by chromatography on a silica column, using as eluent a dichloromethane/methanol mixture (95/5).

Yield: 80%

| Elemental microanalysis: | | | |
|---|---|---|---|
| | C % | H % | N % |
| Calculated | 71.47 | 6.87 | 12.83 |
| Found | 71.09 | 6.82 | 12.70 |

Proton Nuclear Magnetic Resonance (CDC$l_3$/TMS):

The coupling constant J for the two geminate protons 3α and 4α in pyrrolidine is equal to 7.5 Hz.

Stage D:
[(3α,4α)-1-Methyl-4-(4-fluorophenyl)pyrrolidin-3-yl]acetaldehyde

The expected product is obtained using the same procedure as that described in stage A of Example 1.

Yield: 60%

| Elemental microanalysis: | | | |
|---|---|---|---|
| | C % | H % | N % |
| Calculated | 70.57 | 7.29 | 6.33 |
| Found | 70.64 | 7.48 | 6.20 |

Proton Nuclear Magnetic Resonance (CDCl$_3$/TMS)

The coupling constant J for the two geminate protons 3α and 4α in pyrrolidine is equal to 7.5 Hz.

Stage E:
(5Z)-7-[(3α,4α)-1-Methyl-4-(4-fluorophenyl)pyrrolidin-3-yl]hept-5-enoic acid The expected product is obtained according to the same procedure as that described in stage B of Example 1, using the corresponding products.

| Elemental microanalysis: | | | |
|---|---|---|---|
| | C % | H % | N % |
| Calculated | 70.79 | 7.92 | 4.59 |
| Found | 70.40 | 7.88 | 4.29 |

EXAMPLE 6 A: (5Z)-7-[(3α,4α)-1-METHYL-4-(4-FLUOROPHENYL)PYRROLIDIN-3-YL]HEPT-5-ENOIC ACID, SODIUM SALT

Example 6 A is the same as Example 6 but it is obtained using a different procedure.

Stage A:
(3α,4α)-1-Methyl-3-hydroxymethyl-4-(4-fluorophenyl)pyrrolidine

This stage is identical to stage A of Example 6.

Stage B:
(3α,4α)-1-Methyl-3-(para-toluene-sulfonyloxy)methyl-4-(4-fluorophenyl)pyrrolidine To 95 mmol of the compound obtained in the preceding stage, in 300 ml of pyridine, are added, at +10° C., 104 mmol of paratoluenesulfonyl chloride. The mixture is stirred overnight at room temperature and then hydrolyzed with 1.2 l of ice cold water. After extraction with dichloromethane, drying and evaporation, the expected product is recrystallized from an isopropyl ether/ethyl ether mixture.

Yield: 75%

| Elemental microanalysis: | | | |
|---|---|---|---|
| | C % | H % | N % |
| Calculated | 62.74 | 6.05 | 3.85 |
| Found | 62.41 | 5.97 | 3.72 |

Stage C: (3α,4α)-1-Methyl-3-cyanomethyl-4-(4-fluorophenyl)pyrrolidine

Into 20 ml of dimethyl sulfoxide, are added 13 mmol of the product obtained in the preceding stage and 13 mmol of potassium cyanide. The mixture is heated at 110° C. for 15 hours. After evaporation, the residue is taken up in water and extracted with dichloromethane. The expected product is then purified by chromatography on a silica gel, using as eluent a dichloromethane/methanol mixture (95/5).

Stages D And E

These stages are identical to stages D and E of Example 6 and give the same compounds.

Examples 7 to 12 are obtained according to the procedure described in Examples 6 or 6A, using the corresponding starting materials.

EXAMPLE 7:
(4Z)-6-[(3α,4α)-1-METHYL-4-(4-FLUOROPHENYL) PYRROLIDIN-3-YL]HEX-4-ENOIC ACID

| Elemental microanalysis: | | | |
|---|---|---|---|
| | C % | H % | N % |
| Calculated | 70.08 | 7.61 | 4.81 |
| Found | 69.87 | 8.12 | 5.03 |

EXAMPLE 8: (4Z)-6-[(3α,4α)-1-METHYL-4-(2-METHYOXYPHENYL)PYRROLIDIN-3-YL]HEX-4-ENOIC ACID

EXAMPLE 9: (4Z)-6-[(3α,4α)-1-BENZYL-4-(2-METHOXYPHENYL)PYRROLIDIN-3-YL]HEX-4-ENOIC ACID

EXAMPLE 10: (4Z)-6-[(3α,4β)-1-METHYL-4-PHENYLPYRROLIDIN-3-YL]HEX-4-ENOIC ACID, SODIUM SALT

| Elemental microanalysis: | | | |
|---|---|---|---|
| | C % | H % | N % |
| Calculated | 67.02 | 7.56 | 4.59 |
| Found | 66.88 | 6.88 | 4.50 |

EXAMPLE 11: (5Z)-7-[(3α,4β)-1-METHYL-4-(4-FLUOROPHENYL) PYRROLIDIN-3-YL]HEPT-5-ENOIC ACID

| Elemental microanalysis: | | | |
|---|---|---|---|
| | C % | H % | N % |
| Calculated | 70.79 | 7.92 | 4.59 |
| Found | 70.40 | 7.88 | 4.29 |

EXAMPLE 12: (4Z)-6-[(3α,4β)-1-METHYL-4-(2-METHOXYPHENYL) PYRROLIDIN-3-YL]HEX-4-ENOIC ACID

EXAMPLE 13: (5Z)-6-[(3α,4α)-1-BENZYL-4-(2-HYDROXPHENYL) PYRROLIDIN-3-YL]HEX-5-ENOIC ACID

This compound is obtained using the same procedure as that described for Example 1.

| Elemental microanalysis: | | | |
|---|---|---|---|
| | C % | H % | N % |
| Calculated | 75.59 | 7.45 | 3.83 |
| Found | 75.22 | 7.19 | 3.72 |

EXAMPLE 14: (5Z)-7-[(3α,4α)-1-BENZYL-4-(2-HYDROXYPHENYL) PYRROLIDIN-3-YL]HEPT-5-ENOIC ACID

Stage A:
(3aα,9bα)-2-Benzyl-4-hydroxy-1,2,3,3a,4,9b-hexahydrobenzopyrano[3,4-c]pyrrole To a solution containing 100 mmol of 2-benzyl-4-oxoperhydrobenzopyrano[3,4-c]pyrrolidine (prepared according to the procedure described in Chem. Pharm. Bull., 33, 2762, 1985 and Organic Synthesis, 67, 133, 1988) in 800 ml of toluene, are added, at −75° C., 200 mmol of diisobutylaluminum hydride. The mixture is kept for 45 minutes at −75° C. and then treated for 30 minutes with a solution containing 75 ml of isopropanol and 225 ml of toluene. 300 ml of water are then added and the stirring is continued for 15 hours. The two-phase medium is decanted and filtered. The expected product is extracted from the crude mixture by crystallization from ethyl ether.
Yield: 65%
Melting Point: 138° C.

| Elemental microanalysis: | | | |
|---|---|---|---|
| | C % | H % | N % |
| Calculated | 76.84 | 6.81 | 4.98 |
| Found | 76.78 | 6.95 | 5.06 |

Stage B:
(3α,4α)-1-Benzyl-3-methoxyvinyl-4-(2-hydroxyphenyl)pyrrolidine

To 49.6 mmol of methoxymethyltriphenylphosphonium chloride, in 160 ml of tetrahydrofuran, are slowly added 49.6 ml of a 1M solution of potassium tert-butoxide. After stirring for 1 hour at room temperature, 16.5 mmol of the product obtained in the preceding stage are added. The mixture is allowed to stand for 2 hours at room temperature and 2 hours at +40° C. and then treated with a saturated solution of ammonium chloride. After extraction with ether, drying and evaporation, the expected product is purified by chromatography on a silica gel, using as elution solvent dichloromethane.
Yield: 62%

Stage C:
[(3α,4α)-1-Benzyl-4-(2-hydroxyphenyl)pyrrolidin-3-yl]acetaldehyde

To 20.4 mmol of the compound obtained in the preceding stage, are added 6 ml of water, 12 ml of acetonitrile and 6 ml of trifluoroacetic acid. After refluxing for 2 hours, the solvents are evaporated. 5 ml of water are added to the residue and then sodium hydroxide up to pH 10 and the mixture is kept stirring for 30 minutes. After extraction with dichloromethane, drying and evaporation, the expected product is obtained after chromatography on a silica using as gel, elution solvent a dichloromethane/methanol mixture (98/2).
Yield: 62%

Stage D: (5Z)-7-[(3α,4α)-1-Benzyl-4-(2-hydroxyphenyl)pyrrolidin-3-yl]hept-5-enoic acid The expected product is obtained using the same procedure as that described in stage B of Example 1.

| Elemental microanalysis: | | | |
|---|---|---|---|
| | C % | H % | N % |
| Calculated | 75.96 | 7.70 | 3.69 |
| Found | 75.49 | 7.54 | 3.49 |

EXAMPLE 15: (4Z)-6-[(3α,4α)-1-BENZYL-4-(2-HYDROXYPHENYL) PYRROLIDIN-3-YL]HEX-4-ENOIC ACID

This compound is obtained according to the same procedure as that described in Example 14.

| Elemental microanalysis: | | | |
|---|---|---|---|
| | C % | H % | N % |
| Calculated | 75.59 | 7.45 | 3.83 |
| Found | 75.24 | 7.43 | 4.02 |

EXAMPLE 16: (4Z)-6-[(3α,4α)-1-NICOTINOYL-4-(2-HYDROXYPHENYL) PYRROLIDIN-3-YL]HEX-4-ENOIC ACID

Stage A:
(3aα,9bα)-2-Benzyl-4-hydroxy-1,2,3,3a,4,9b-hexahydrobenzopyrano[3,4-c]pyrrole This stage is identical to stage A of Example 14.

Stage B:
(3aα,9bα)-4-Hydroxy-1,2,3,3a,4,9b-hexahydrobenzopyrano[3,4-c]pyrrole, hydrochloride Debenzylation of the compound obtained in the preceding stage is performed in dioxane, at 60° C. and at atmospheric pressure, in the presence of gaseous hydrochloric acid and 10% by mass of 10% palladium on carbon. The catalyst is then filtered and washed with dimethylformamide. The filtrate is evaporated. The expected product is obtained by converting the oil thus obtained to the hydrochloride in dioxane.
Yield: 90%
Melting Point: 168° C.

Stage C: (3aα,9bα)-2-Nicotinoyl-4-hydroxy-1,2,3,3a,4,9b-hexahydrobenzopyrano[3,4-c]pyrrole To 176 mmol of nicotinic acid chloride, in solution in chloroform, at 0° C., are added 176 mmol of the compound obtained in the preceding stage, in solution in chloroform, in the presence of 352 mmol of triethylamine. After stirring for 3 hours at room temperature, 200 ml of water are added. The chloroformic phase is decanted, washed with acidulated water, dried and evaporated. The expected product is obtained after purification of the oil by chromatography on silica, using as eluent ethyl ether.
Yield: 85%

Stage D:
(3α,4α)-1-Nicotinoyl-3-methoxyvinyl-4-(2-hydroxyphenyl)pyrrolidine

The expected product is obtained according to the same procedure as that described in stage B of Example 14.
Yield: 65%

Stage E:
[(3α,4α)-1-Nicotinoyl-4-(2-hydroxyphenyl)pyrrolidinyl-3-yl]acetaldehyde The expected product is obtained according to the same procedure as that described in stage C of Example 14.
Yield: 80%

Stage F:
(4Z)-6-[3α,4α)-1-Nicotinoyl-4-(2-hydroxyphenyl) pyrrolidin-3-yl]hex-4-enoic acid The expected product is obtained according to the same procedure as that described in stage B of Example 1.

| | Elemental microanalysis: | | |
|---|---|---|---|
| | C % | H % | N % |
| Calculated | 69.47 | 6.31 | 7.37 |
| Found | 69.64 | 6.46 | 7.15 |

EXAMPLES 17 AND 18

EXAMPLE 17:
(4Z)-6-[3α,4α)-1-(4-CHLOROPHENYLSULFONYL)-4-(2-HYDROXYPHENYL)PYRROLIDIN-3-YL]HEX-4-ENOIC ACID

Stage A:
(3aα,9bα)-2-Benzyl-4-hydroxy-1,2,3,3a,4,9b-hexahydrobenzopyrano[3,4-c]pyrrole This stage is identical to stage A of Example 14.

Stage B:
(3aα,9bα)-4-Ethoxy-1,2,3,3a,4,9b-hexahydrobenzopyrano[3,4-c]pyrrole, hydrochloride This stage is identical to stage B of Example 16 but is carried out in ethanol and precipitation of the hydrochloride is carried out in a dioxane/ethyl ether medium.
Yield: 95%

Stage C:
(3α,9bα)-4-Chlorophenylsulfonyl-4-ethoxy-1,2,3,3a,4,9b-benzopyrano[3,4-c]pyrrole The expected product is obtained using the same procedure as that described in stage C of Example 16.
Yield: 85%

Stage D:
(3aα,9bα)-2-(4-Chlorophenylsulfonyl)-4-hydroxy-1,2,3,3a,4,9b-benzopyrano[3,4-c]pyrrole 45 mmol of the product obtained in the preceding stage are hydrolyzed in 40 ml of water in the presence of 40 ml of trifluoroacetic acid and 70 ml of acetonitrile under reflux for 5 hours.
Yield: 90%
Melting Point: 156°–158° C.

Stage E:
(3α,4α)-1-(4-Chlorophenylsulfonyl)-3-methoxyvinyl-4-(2-hydroxyphenyl)pyrrolidine and
(3α,4β)-1-(4-chlorophenylsulfonyl)-3-methoxyvinyl-4-(2-hydroxyphenyl) pyrrolidine The expected products are obtained in the form of a mixture of diastereoisomers using the same procedure as that described in stage B of Example 14.
Yield: 90%

Stage F:
[(3α,4α)-1-(4-Chlorophenylsulfonyl)-4-(2-hydroxyphenyl)pyrrolidin-3-yl]acetaldehyde and [(3α,4β)-1-(4-chlorophenylsulfonyl)-4-(2-hydroxyphenyl)-pyrrolidin-3-yl]acetaldehyde The expected products are obtained using the same procedure as that described in stage C of Example 14, using the preceding mixture as starting material.
Yield: 90%

Stage G:
(4Z)-6-[(3α,4α)-1-(4-Chlorophenylsulfonyl)-4-(2-hydroxyphenyl)pyrrolidin-3-yl]hex-4-enoic acid The expected product is obtained using the same procedure as that described in stage B of Example 1, followed by HPLC separation under the following conditions: column: Lichrosorb RP18; elution eluent: methanol/water/perchloric acid: 55/45/0.05.
Yield: 35%

| Elemental microanalysis: | | | | |
|---|---|---|---|---|
| | C % | H % | N % | Cl % | S % |
| Calculated | 58.73 | 5.38 | 3.11 | 7.88 | 7.13 |
| Found | 58.62 | 5.82 | 3.16 | 8.11 | 6.85 |

EXAMPLE 18: (4Z)-6-[(3α,4β)-1-(4-Chlorophenylsulfonyl)-4-(2-HYDROXYPHENYL)PYRROLIDIN-3-YL]HEX-4-ENOIC ACID The expected product is obtained in the HPLC separation described in stage G of Example 17.

EXAMPLES 19 AND 20

EXAMPLE 19: (4Z)-6-[(3α,4α)-1-ISOBUTYROYL-4-(2-HYDROXYPHENYL) PYRROLIDIN-3-YL)]HEX-4-ENOIC ACID

Stage A:
(3aα,9bα)-2-Benzyl-4-hydroxy-1,2,3,3a,4,9b-hexahydrobenzopyrano[3,4-c]PYRROLE The expected product is obtained according to the same procedure as that described in stage A of Example 14.

Stage B:
(3aα,9bα)-4-Hydroxy-1,2,3,3a,4,9b-hexahydrobenzopyrano[3,4-c]pyrrole, hydrochloride The expected product is obtained according to the same procedure as that described in stage B of Example 16.

Stage C:
(3aα,9bα)-2-Isobutyroyl-4-hydroxy-1,2,3,3a,4,9b-hexahydrobenzopyrano[3,4-c]pyrrole The expected product is obtained according to the same procedure as that described in stage C of Example 16, replacing nicotinic acid chloride with isobutyric acid chloride.
Yield: 90%

Stage D:
(3α,4α)-1-Isobutyroyl-3-methoxyvinyl-4-(2-hydroxyphenyl)pyrrolidine and
(3α,4β)-1-isobutyroyl-3-methoxyvinyl-4-(2-hydroxyphenyl)pyrrolidine The expected products are obtained in the form of a mixture of diastereoisomers using the same procedure as that described in stage B of Example 14.
Yield: 75%

Stage E: [(3α,4α)-1-Isobutyroyl-4-(2-hydroxyphenyl) pyrrolidinyl-3-yl]acetaldehyde and
[(3α,4β)-1-isobutyroyl-4-(2-hydroxyphenyl) pyrrolidinyl-3-yl]acetaldehyde The expected products are obtained using the same procedure as that described in stage C of Example 14, using the preceding mixture as starting material.
Yield: 85%

Stage F:
(4Z)-6-[(3α,4α)-1-Isobutyroyl-4-(2-hydroxyphenyl)pyrrolidin-3-yl)]hex-4-enoic acid The expected product is obtained according to the same procedure as that described in stage B of Example 1 and is purified by HPLC (C18 reversed-phase), using as eluent a methanol/water/perchloric acid mixture (55/45/0.05).

| Elemental microanalysis: | | | |
|---|---|---|---|
| | C % | H % | N % |
| Calculated | 69.54 | 7.88 | 4.05 |
| Found | 69.01 | 7.55 | 3.94 |

EXAMPLE 20: (4Z)-6-[(3α,4β)-1-ISOBUTYROYL-4-(2-HYDROXYPHENYL) PYRROLIDIN-3-YL]HEX-4-ENOIC ACID

The expected product is obtained in the HPLC separation described in stage F of Example 19.

Proton Nuclear Magnetic Resonance (Pyridine/TMS)

The coupling constant J for the two ethylenic protons is equal to 10.8 Hz.

EXAMPLE 21: (4Z)-6-[(3α,4α)-4-(2-HYDROXYPHENYL)-1-[(3-PYRIDYL) METHYL]PYRROLIDIN-3-YL]HEX-4-ENOIC ACID

Stage A:
(3aα,4bα)-2-[(3-pyridyl)methyl]-4-oxoperhydrobenzopyrano[3,4-c]pyrrolidine This compound is prepared according to the procedure described in Chem. Pharm. Bull., 33, 2762, 1985 and Organic Synthesis, 67., 133, 1988, by replacing benzylamine with 3-aminomethylpyridine.
Yield: 65%
Melting Point: 70°–72° C.

| Elemental microanalysis: | | | |
|---|---|---|---|
| | C % | H % | N % |
| Calculated | 72.84 | 5.75 | 9.99 |
| Found | 72.10 | 5.49 | 10.03 |

Stage B:
(3aα,9bα)-2-[(3-Pyridyl)methyl]-4-hydroxy-1,2,3,3a,4,9b-hexahydrobenzopyrano[3,4-c]pyrrole The expected product is obtained according to the same procedure as that described in stage A of Example 14.
Yield: 80%

| Elemental microanalysis: | | | |
|---|---|---|---|
| | C % | H % | N % |
| Calculated | 72.32 | 6.43 | 9.92 |
| Found | 72.91 | 6.81 | 9.56 |

Stage C:
(3α,4α)-1-(3-Pyridyl)methyl-3-methoxyvinyl-4-(2-hydroxyphenyl)pyrrolidine The expected product is obtained according to the same procedure as that described in stage B of Example 14.
Yield: 70%

Stage D:
[(3α,4α)-1-(3-Pyridyl)methyl-4-(2-hydroxyphenyl)pyrrolidinyl-3-yl]acetaldehyde The expected product is obtained according to the same procedure as that described in stage C of Example 14.
Yield: 45%

Stage E:
(4Z)-6-[(3α,4β)-4-(2-Hydroxyphenyl-1-[(3-pyridyl)methyl]pyrrolidin-3-yl]hex-4-enoic acid The expected product is obtained according to the same procedure as that described in stage B of Example 1.
Yield: 40%

| | Elemental microanalysis: | | |
|---|---|---|---|
| | C % | H % | N % |
| Calculated | 72.11 | 7.15 | 7.64 |
| Found | 72.28 | 6.83 | 7.84 |

EXAMPLE 22:
(4Z)-6-[(3α,4α)-1-PHENYLAMINOCARBONYL-4-(2-HYDROXYPHENYL)PYRROLIDIN-3-YL]HEX-4-ENOIC ACID

Stage A:
(3aα,9bα)-2-Benzyl-4-hydroxy-1,2,3,3a,4,9b-hexahydrobenzopyrano[3,4-c]pyrrole The expected product is obtained according to the same procedure as that described in stage A of Example 14.

Stage B:
(3aα,9bβ)-4-Hydroxy-1,2,3,3a,4,9b-hexahydrobenzopyrano[3,4-c]pyrrole, hydrochloride The expected product is obtained according to the same procedure as that described in stage B of Example 16.

Stage C: (3aα,9bα)
-4-Phenylaminocarbonyl-4-ethoxy-1,2,3,3a,4,9b-hexahydrobenzopyrano[3,4-c]pyrrole The expected product is obtained using the same procedure as that described in stage C of Example 16.
Yield: 60%

Stage D:
(3aα,9bα)-4-Phenylaminocarbonyl-4-hydroxy-1,2,3,3a,4,9b-hexahydrobenzopyrano[3,4-c]pyrrole The expected product is obtained using the same procedure as that described in stage D of Example 17.
Yield: 60%
Melting Point: 238°–240° C.

Stage E:
(3α,4α)-1-Phenylaminocarbonyl-3-methoxyvinyl-4-(2-hydroxyphenyl)pyrrolidine The expected product is obtained using the same procedure as that described in stage B of Example 14.
Yield: 75%

Stage F:
[(3α,4α)-1-Phenylaminocarbonyl-4-(2-hydroxyphenyl)pyrrolidin-3-yl]acetaldehyde The expected product is obtained using the same procedure as that described in stage C of Example 14.
Yield: 95%

Stage G:
(4Z)-6-[(3α,4α)-1-Phenylaminocarbonyl-4-(2-hydroxyphenyl)pyrrolidin-3-yl]hex-4-enoic acid The expected product is obtained using the same procedure as that described in stage B of Example 1.
Yield: 55%

| | Elemental microanalysis: | | |
|---|---|---|---|
| | C % | H % | N % |
| Calculated | 69.85 | 6.88 | 7.08 |
| Found | 69.75 | 6.89 | 7.10 |

EXAMPLE 23:
(4Z)-6-[(3α,4α)-1-HEPTANOYL-4-(2-HYDROXYPHENYL) PYRROLIDIN-3-YL]HEX-4-ENOIC ACID

This compound is obtained according to the same procedure as that described in Example 16.
Yield: 36%

EXAMPLES 24 AND 25

EXAMPLE 24:
(4Z)-6-[(3α,4α)-1-[(ISOQUINOL-5-YL)SULFONYL]-4-(2-HYDROXYPHENYL)PYRROLIDIN-3-YL]HEX-4-ENOIC ACID

This compound is obtained according to the same procedure as that described in Example 19.
Yield: 25%

| | Elemental microanalysis: | | | |
|---|---|---|---|---|
| | C % | H % | N % | S % |
| Calculated | 64.36 | 5.62 | 6.00 | 6.87 |
| Found | 64.11 | 5.54 | 6.11 | 6.75 |

EXAMPLE 25:
(4Z)-6-[(3α,4β)-1-[(ISOQUINOL-5-YL)SULFONYL]-4-(2-HYDROXYPHENYL)PYRROLIDIN-3-yl]HEX-4-ENOIC ACID

The expected product is obtained in the HPLC separation of the compound of Example 24.
Yield: 20%

EXAMPLE 26:
4Z-6-[1-(4-CHLOROPHENYLSULFONYL)PYRROLIDIN-3-YL]HEX-4-ENOIC ACID

Stage A: 3-Cyanomethylpyrrolidine Hydrochloride

Catalytic debenzylation, in the presence of hydrogen and palladised carbon, of 3-cyanomethyl-1-benzylpyrrolidine hydrochloride, in ethanol, makes it possible to obtain the desired compound.
Yield: 95%

Stage B:
3-Cyanomethyl-1-(4-chlorophenylsulfonyl)pyrrolidine

Acylation, in chloroform, of 36.6 g (0.25 mol) of 3-cyanomethylpyrrolidine hydrochloride with 52.7 g (0.25 mol) of para-chlorophenylsulfonic acid chloride, in the presence of 50.5 g (0.5 mol) of triethylamine makes it possible to obtain 72 g of a solid which is purified by chromatography on silica, Merck 70-230 mesh, using as eluent a dichloromethane/methanol mixture (99/1 v/v).
Yield: 65%

Stage C:
[1-(4-Chlorophenylsulfonyl)pyrrolidin-3-yl]acetaldehyde 10 g (0.035 mol) of the compound obtained in the preceding stage are dissolved in 150 ml of dichloromethane cooled to −60° C. 159 ml of 1M diisobutylaluminum hydride, in hexane, are added to this solution and then the mixture is hydrolyzed 2 hours later with 67 ml of methanol, 1 l of ethyl ether, 67 ml of a saturated solution of sodium chloride and 48 g of sodium sulfate. After filtration and concentration, 10 g of the desired aldehyde are obtained.
Yield: 100%

Stage D:
(R,S)-4Z-6-[1-(4-Chlorophenylsulfonyl)pyrrolidin-3-yl]hex-4-enoic acid The expected product is obtained according to the same procedure as that described in stage B of Example 1, but using 2 mol of 3-carboxypropyltriphenylphosphonium bromide and 4 mol of potassium tert-butoxide for 1 mol of the compound of the preceding stage.

| Elemental microanalysis: | | | | | |
|---|---|---|---|---|---|
| | C % | H % | N % | Cl % | S % |
| Calculated | 53.70 | 5.63 | 3.91 | 9.91 | 8.96 |
| Found | 53.99 | 5.74 | 4.22 | 9.62 | 9.01 |

EXAMPLE 27:
(4Z)-6-[(3α,4α)-1-[(QUINOL-8-YL)SULFONYL]-4-(2-HYDROXYPHENYL)PYRROLIDIN-3-YL]HEX-4-ENOIC ACID

This compound is obtained according to the same procedures as those described in Example 28.
Yield: 30%

| Elemental microanalysis: | | | | |
|---|---|---|---|---|
| | C % | H % | N % | S % |
| Calculated | 64.36 | 5.62 | 6.00 | 6.87 |
| Found | 64.22 | 5.88 | 6.12 | 6.62 |

EXAMPLE 28: (4Z) -6-[(3α,4α) -1-NAPHTH-1-YLSULFONYL)-4-(2-HYDROXYPHENYL)PYRROLIDIN-3-YL)]HEX-4-ENOIC ACID

Stage A:
(3α,4α)-1-Benzyl-3-hydroxymethyl-4-(2-methoxyphenyl) pyrrolidine

The expected product is obtained according to the same procedure as that described in stage A of Example 6, but using methyl [(3α,4α)-1-benzyl-4-(2-methoxyphenyl)pyrrolidin-3-yl]carboxylate (prepared according to the procedure described in J. Chem. Soc., Chem. Comm., 1566, 1985) as starting material.
Yield: 93%
Melting Point: 75%

| Elemental microanalysis: | | | |
|---|---|---|---|
| | C % | H % | N % |
| Calculated | 76.74 | 7.80 | 4.71 |
| Found | 76.78 | 7.82 | 5.07 |

Stage B:
(3α,4α)-1-Benzyl-3-chloromethyl-4-(2-methoxyphenyl) pyrrolidine

The expected product is obtained according to the same procedure as that described in stage B of Example 6.
Yield: 93%
Melting Point: 207°-209° C. (Hydrochloride)

| Elemental microanalysis (hydrochloride): | | | | | |
|---|---|---|---|---|---|
| | C % | H % | N % | Cl % | Cl % |
| Calculated | 64.78 | 6.58 | 3.98 | 20.13 | 10.06 |
| Found | 64.59 | 6.46 | 4.01 | 20.21 | 10.02 |

Stage C:
(3α,4α)-1-Benzyl-3-cyanomethyl-4-(2-methoxyphenyl) pyrrolidine

The expected product is obtained according to the same procedure as that described in stage C of Example 6.
Yield: 90%

| Elemental microanalysis: | | | |
|---|---|---|---|
| | C % | H % | N % |
| Calculated | 78.40 | 7.24 | 9.14 |
| Found | 78.45 | 7.17 | 9.18 |

Stage D:
(3α,4α)-3-Cyanomethyl-4-(2-methoxyphenyl)pyrrolidine

Debenzylation of the compound obtained in the preceding stage is performed in ethanol, at 30° C. and at atmospheric pressure, in the presence of gaseous hydrochloric acid and 10% by mass of 10% palladised carbon. The catalyst is then filtered, the filtrate evaporated and the crystals are filtered.
Yield: 98%

Stage E:
(3α,4α)-1-(Naphth-1-ylsulfonyl)-3-cyanomethyl-4-(2-methoxyphenyl)pyrrolidine The expected product is obtained according to the same procedure as that described in stage C of Example 16.
Yield: 85%

Stage F:
(3α,4α)-1-(Naphth-1-ylsulfonyl)-3-cyanomethyl-4-(2-hydroxyphenyl)pyrrolidine 240 ml (0.24 mol) of a 1M solution of boron tribromide, in dichloromethane, are added, at −30° C., to a chloroformic solution of 20.5 g (0.0475 mol) of the compound obtained in the preceding stage. After 12 hours at room temperature, 100 ml of water and then 90 ml of caustic soda are added at 10° C.. The organic phase is decanted at pH 7 and it is then evaporated after drying over sodium sulfate. The product is purified by chromatography on silica, using as eluent a dichloromethane/methanol mixture (98/2 v/v).
Yield: 45%

Stage G:
[(3α,4α)-1-(Naphth-1-ylsulfonyl)-4-(2-hydroxyphenyl)pyrrolidin-3-yl]acetaldehyde The expected product is obtained according to the same procedure as that described in stage A of Example 1.
Yield: 75%

Stage H:
(4Z)-6-[(3α,4α)-1-(Naphth-1-ylsulfonyl)-4-(2-hydroxyphenyl)pyrrolidin-3-yl)]hex-4-enoic acid The expected product is obtained according to the same procedure as that described in stage B of Example 1.
Yield: 25%

| | Elemental microanalysis: | | | |
|---|---|---|---|---|
| | C % | H % | N % | S % |
| Calculated | 67.08 | 5.85 | 3.01 | 6.89 |
| Found | 66.80 | 6.10 | 2.89 | 6.58 |

EXAMPLE 29:
(4Z)-6-[(3α,4α)-1-(NAPHTH-2-YLSULFONYL)-4-(2-HYDROXYPHENYL)PYRROLIDIN-3-YL)]HEX-4-ENOIC ACID

This compound is obtained according to the same procedures as those described in Example 28.
Yield: 25%

| | Elemental microanalysis: | | | |
|---|---|---|---|---|
| | C % | H % | N % | S % |
| Calculated | 67.08 | 5.85 | 3.01 | 6.89 |
| Found | 66.81 | 6.01 | 3.14 | 7.21 |

EXAMPLE 30: (5Z)
-7-[(3α,4α)-1-[(ISOQUINOLYL-5-YL)SULFONYL]-4-(2-HYDROXYPHENYL)PYRROLIDIN-3-YL)]HEPT-5-ENOIC ACID

This compound is obtained according to the same procedures as those described in Example 28.
Yield: 20%

| | Elemental microanalysis: | | | |
|---|---|---|---|---|
| | C % | H % | N % | S % |
| Calculated | 64.98 | 5.87 | 5.83 | 6.67 |
| Found | 64.66 | 6.15 | 5.68 | 6.67 |

EXAMPLE 31:
(4Z)-6-[(3α,4α)-1-(NAPHTH-1-YLSULFONYL)-4-(2-HYDROXY-5-METHYLPHENYL)PYRROLIDIN-3-YL]HEX-4-ENOIC ACID

Stage A:
(3α,4α)-1-Benzyl-3-hydroxymethyl-4-(2-methoxy-5-methyl phenyl)pyrrolidine The expected product is obtained by the same procedure as that described in stage A of Example 6, the starting material being methyl [(3α,4α)-1-benzyl-4-(2-methoxy-5-methylphenyl) pyrrolidin-3-yl] carboxylate (prepared according to the same procedure as that described in J. Chem. Soc., Chem. Comm., 1566, 1985).
Yield: 93%

| | Elemental microanalysis: | | |
|---|---|---|---|
| | C % | H % | N % |
| Calculated | 77.14 | 8.09 | 4.50 |
| Found | 76.86 | 7.99 | 4.32 |

Stage B:
(3α,4α)-1-Benzyl-3-chloromethyl-4-(2-methoxy-5-methylphenyl)pyrrolidine The expected product is obtained according to the same procedure as that described in stage B of Example 6.
Yield: 82%

| | Elemental microanalysis: | | | |
|---|---|---|---|---|
| | C % | H % | N % | Cl % |
| Calculated | 72.82 | 7.33 | 4.25 | 10.75 |
| Found | 72.62 | 7.10 | 4.36 | 11.02 |

Stage C:
(3α,4α)-1-Benzyl-3-cyanomethyl-4-(2-methoxy-5-methylphenyl)pyrrolidine The expected product is obtained according to the same procedure as that described in stage C of Example 6.
Yield: 63%

| | Elemental microanalysis: | | | |
|---|---|---|---|---|
| | C % | H % | N % | S % |
| Calculated | 68.55 | 5.75 | 6.66 | 7.62 |
| Found | 68.28 | 5.82 | 6.42 | 7.73 |

Stage D:
(3α,4α)-3-Cyanomethyl-4-(2-methoxy-5-methylphenyl)pyrrolidine

The expected product is obtained according to the same procedure as that described in stage D of Example 28.

Stage E:
(3α,4α)-1-(Naphth-1-ylsulfonyl)-3-cyanomethyl-4-(2-methoxy-5-methylphenyl)pyrrolidine The expected product is obtained according to the same procedure as that described in stage C of Example 16.
Yield: 78%

Stage F:
(3α,4α)-1-(Naphth-1-ylsulfonyl)-3-cyanomethyl-4-(2-hydroxy-5-methylphenyl)pyrrolidine The expected product is obtained according to the same procedure as that described in stage F of Example 28.
Yield: 62%

|  | Elemental microanalysis: | | | |
|---|---|---|---|---|
|  | C % | H % | N % | S % |
| Calculated | 67.96 | 5.45 | 6.89 | 7.88 |
| Found | 67.72 | 5.58 | 6.71 | 7.63 |

Stage G:
[(3α,4α)-1-(Naphth-1-ylsulfonyl)-4-(2-hydroxy-5-methylphenyl)pyrrolidin-3-yl]acetaldehyde The expected product is obtained according to the same procedure as that described in stage A of Example 1.
Yield: 78%

Stage H:
(4Z)-6-[(3α,4α)-1-(Naphth-1-ylsulfonyl)-4-(2-hydroxy-5-methylphenyl)pyrrolidin-3-yl]hex-4-enoic acid The expected product is obtained according to the same procedure as that described in stage B of Example 1.
Yield: 38%

|  | Elemental microanalysis: | | | |
|---|---|---|---|---|
|  | C % | H % | N % | S % |
| Calculated | 67.62 | 6.09 | 2.92 | 6.68 |
| Found | 67.35 | 5.89 | 3.07 | 6.74 |

EXAMPLE 32:
(4Z)-6-[(3α,4α)-1-(NAPHTH-1-YLSULFONYL)-4-(2-METHOXY-5-METHYLPHENYL)PYRROLIDIN-3-YL]HEX-4-ENOIC ACID

Stages A, B, C, D and E are identical to stages A, B, C, D and E of Example 31.

Stage F:
[(3α,4α)-1-(Naphth-1-ylsulfonyl)-4-(2-methoxy-5-methylphenyl)pyrrolidin-3-yl]acetaldehyde The expected product is obtained according to the same procedure as that described in stage A of Example 1.
Yield: 83%

Stage G:
(4Z)-6-[(3α,4α)-1-(Naphth-1-ylsulfonyl)-4-(2-methoxy-5-methylphenyl)pyrrolidin-3-yl]hex-4-enoic acid The expected product is obtained according to the same procedure as that described in stage B of Example 1.
Yield: 36%

|  | Elemental microanalysis: | | | |
|---|---|---|---|---|
|  | C % | H % | N % | S % |
| Calculated | 68.13 | 6.33 | 2.84 | 6.49 |
| Found | 68.02 | 6.41 | 2.68 | 6.55 |

PHARMACOLOGICAL STUDY OF THE COMPOUNDS OF THE INVENTION

EXAMPLE 33: PLATELET AGGREGATION

The rabbits (2–3 kg) are anesthetized with sodium pentobarbital (30 mg/kg i.v.). After cannulation of the left carotid artery, the blood is collected over sodium citrate (0.109M) (1 vol. of citrate per 9 vol. of blood).

The plasma which is high in platelets (PRP) is obtained by centrifugation (20° C.) at 250 g for 20 minutes and the plasma which is low in platelets (PPP) by centrifugation at 1000 g (10 min). The number of platelets (PL) in the PRP is adjusted to between 300–350,000 pl/mm$^3$ by dilution with autologous PPP. The PRP is stored at room temperature up to the time of the test and is used within 4 hours following the collection.

Platelet aggregation is performed at 37° C. in glass tubes siliconized by means of an aggregometer. The PRP and PLs are stirred at 1000 rpm (revolution per minute). In order to study the activity of the thromboxane antagonists, the PRP is incubated for 1 min at 37° C., and the antagonist is then added for a period of 3 min before adding the agonist U46619 (1.2 μM). The final volume of the cuvette is then 250 μl. The extent of platelet aggregation is determined by measuring the maximum amplitude of the aggregation plots and is expressed as a percentage of light transmission (% T). The activity of the antagonists is expressed as IC$_{50}$, that is to say the concentration of the substance which induces 50% inhibition of the aggregation response induced by U46619.

In this test, the IC$_{50}$ of the compounds of Examples 18, 22, 24, 25, 28 and 30 are as follows:
Example 18: 5.4 10$^{-6}$M
Example 22: 4 10$^{-6}$M
Example 24: 0.8 10$^{-6}$M
Example 25: 5 10$^{-6}$M
Example 28: 0.5 10$^{-6}$M
Example 30: 0.5 10$^{-6}$M

EXAMPLE 34: DETERMINATION OF THE pA$_2$ VALUES ON GUINEA PIG TRACHEA

400–500-gram albino male guinea pigs were sacrificed by striking the nape of the neck and by pulling the neck. The throat is cut and the trachea is rapidly removed and then cut out into rings containing two cartilages. These rings are mounted between two hooks in cuvettes thermostated at 37° C., containing physiological saline (composition in mM: 118 NaCl; 25 NaHCO$_3$; 10 glucose; 4.7 KCl; 1.25 CaCl$_2$; 1.19 MgSO$_4$; 1.14 KH$_2$PO$_4$).

The physiological saline is bubbled with a mixture of 95% O$_2$ - 5% CO$_2$. The bottom hook constitutes the fixed point while the upper hook is connected to an isometric force sensor. The tissues are placed under a basal tension of 3.5 grams. The pharmacological substances studied are prepared immediately before use. The drugs are solubilized in water or in dimethyl sulfoxide.

After mounting, the preparations are allowed to stand for 90 minutes, rinsings being carried out every 30 minutes. After readjusting the basal tension, a contraction generated by a single dose of agonist (U46619; 10$^{-5}$M) is generated in order to stabilize subsequent contractions. After washing and returning to the base line, a first effect/concentration curve is produced by the addition of cumulative doses of U46619 (10$^{-9}$M to 10$^{-5}$M; the interval between the doses is a semilog).

This first experiment makes it possible to calculate the effective concentration 50% ($EC_{50}$) "control".

This $EC_{50}$ is routinely calculated in the following manner: the tension values are first converted to percentages relative to the maximum effect, these percentages are then plotted on a graph with the percentages on the y-axis and the log(concentration) values on the x-axis. A linear regression is then performed on the points between 10% and 90% (which corresponds to the linear portion of the sigmoid curve). The concentration corresponding to half maximum effect (50%) can be easily calculated by means of the parameters of the straight line.

After washing and returning to the base line, the organ is placed in contact with the antagonist (8 different concentrations for each organ) for 20 minutes. A second effect/concentration curve is then produced in the presence of the antagonist and the "treated" $EC_{50}$ can then be calculated. All the elements required for calculating the $pA_2$ (competitive antagonism) or the $pD_2$ (noncompetitive antagonism) are thus available.

The $pA_2$ (which represents the negative logarithm of the concentration of antagonist in the presence of which twice the amount of agonist is required in order to obtain the same effect) is determined by plotting on a graph the log((L/1)-1) values relative to the log(concentration of antagonist), with L=effect in the presence of antagonist and 1=control effect.

In this test, the $pA_2$ values for the compounds of Examples 14 and 18 are as follows:

Example 14: 6.55
Example 18: 8.10
Example 19: 6.7
Example 21: 5.8
Example 23: 7.7
Example 24: 9.5
Example 28: 8.8

EXAMPLE 35: $IC_{50}$ ON THE TRACHEAL PRESSURE IN GUINEA PIGS

Male albino guinea pigs (350–400 g), subjected to an 18-hour water diet, are anesthetized with ethylcarbamate (1.25 g/kg i.p.). A catheter is introduced into the carotid artery in order to measure the blood pressure by means of a pressure cell. A second catheter is introduced introduced into the jugular vein and is used for injecting the pharmacological substances. The trachea is cannulated and the guinea pig is placed under assisted respiration by means of a respirator. The temperature of the animal is kept at 37° C. by means of a thermostated cover. A needle pricked into the tracheal cannula is connected to a pressure cell and allows the tracheal pressure to be recorded. The guinea pigs are pretreated with d-tubocurarine (1 mg/kg i.v.) and with indomethacin (10 mg/kg i.v.). Injected at a dose of 2 µg/kg i.v., U46619 causes a bronchoconstriction which results in an increase in tracheal pressure and induces an increase in blood pressure. The responses to U46619 are reversible and reproducible if the injections are performed every 10 minutes.

The antagonists of thromboxane receptors are injected 5 minutes before the injections of U46619. The antagonist dose which inhibits by 50% the increase in tracheal pressure caused by U46619 is determined ($IC_{50}$).

Example 13: 2.28 mg/kg
Example 14: 1.02 mg/kg
Example 15: 0.177 mg/kg
Example 18: 0.030 mg/kg
Example 19: 0.1 mg/kg
Example 20: 1.31 mg/kg
Example 21: 1.03 mg/kg
Example 22: 1.21 mg/kg
Example 23: 0.43 mg/kg
Example 24: 0.01 mg/kg
Example 25: 0.06 mg/kg
Example 27: 0.03 mg/kg
Example 28: 0.01 mg/kg
Example 29: 0.11 mg/kg
Example 30: 0.08 mg/kg

EXAMPLE 36: PHARMACEUTICAL COMPOSITION

Preparation formula for 1000 tablets in 10 mg doses

| | |
|---|---|
| Compound of Example 1 | 10 g |
| Hydroxypropyl cellulose | 2 g |
| Wheat starch | 10 g |
| Lactose | 100 g |
| Magnesium stearate | 3 g |
| Talc | 3 g |

We claim:
1. A compound selected from those of formula (I):

$$\underset{R_1}{\underset{|}{N}}\diagdown\overset{R_2\quad R_3}{\diagup} \quad (I)$$

in which:
$R_1$ represents:
  phenylsulfonyl (which is unsubstituted or substituted on the phenyl ring by one or more halogen or linear or branched ($C_1$-$C_6$)alkyl, linear or branched ($C_1$-$C_6$)alkoxy or trihalomethyl), naphthylsulfonyl, quinolylsulfonyl, or isoquinolylsulfonyl,
$R_2$ represents:
  hydrogen,
  phenyl which is unsubstituted or substituted by one or more halogen or linear or branched ($C_1$-$C_6$)alkyl, linear or branched ($C_1$-$C_6$)alkoxy, hydroxyl, or trihalomethyl,
  3-pyridyl or 2-pyridyl which is unsubstituted or substituted on the pyridine ring by one or more halogen or linear or branched ($C_1$-$C_6$)alkyl, linear or branched ($C_1$-$C_6$)alkoxy, or trihalomethyl,
$R_3$ represents one of the following groups:

$$\diagup\!\!\!=\!\!\!\diagdown(CH_2)_m\!\!-\!\!CO_2R$$

$$\diagup\!\!\!\diagdown\!\!\!=\!\!\!\diagup(CH_2)_m\!\!-\!\!CO_2R$$

$$-(CH_2)_n-CO_2R$$

in which
m is equal to 2, 3 or 4,
n is equal to 4, 5, 6 or 7,
and R represents hydrogen or a linear or branched ($C_1$-$C_6$) alkyl, its enantiomers, diastereoisomers and epimers, as well as its addition salts with a pharmaceutically acceptable acid or base.

2. A compound of claim 1, selected from those in which $R_1$ represents a substituted or unsubstituted phenylsulfonyl group, its enantiomers, diastereoisomers and epimers, as well as its addition salts with a pharmaceutically-acceptable acid or base.

3. A compound of claim 1, selected from the in which $R_1$ represents naphthylsulfonyl, its enantiomers, diastereoisomers and epimers as well as its addition salts with a pharmaceutically-acceptable acid or base.

4. A compound of claim 1 selected from the in which $R_1$ represents isoquinolylsulfonyl, its enantiomers, diastereoisomers and epimers, as well as its addition salts with a pharmaceutically-acceptable acid or base.

5. A compound of claim 1 selected from the which is (4Z)-6-[3α,4α)-1-(4-chlorophenylsulfonyl)-4-(2-hydroxyphenyl) pyrrolidin-3-yl]hex-4-enoic acid and its salts with a pharmaceutically acceptable acid or base.

6. A compound of claim 1 selected from the which is (4Z)-6-[(3α,4α)-1-[(Isoquinol-5-yl)sulfonyl]-4-(2-hydroxyphenyl)pyrrolidin-3-yl]hex-4-enoic acid and its salts with a pharmaceutically acceptable acid or base.

7. A compound of claim 1 selected from the which is (4Z)-6-[(3α,4α)-1-Naphth-1-ylsulfonyl)-4-(2-hydroxyphenyl) pyrrolidin-3-yl)]hex-4-enoic acid and its salts with a pharmaceutically-acceptable acid or base.

8. A pharmaceutical composition comprising as active principle an effective amount of a compound as claimed in claim 1, together with one or more pharmaceutically-acceptable excipients or vehicles.

* * * * *

UNITED STATES PATENT AND TRADEMARK OFFICE
CERTIFICATE OF CORRECTION

PATENT NO. : 5,387,591

DATED : February 7, 1995

Page 1 of 3

INVENTOR(S) : Gilbert Lavielle, Thierry Dubuffet, Olivier Muller, Michel Laubie, Tony Verbeuren It is certified that error appears in the above-indentified patent and that said Letters Patent is hereby corrected as shown below:

Column 5, line 57; (in the formula) the "$R_2'$" should read -- $R'_2$ --
Column 6, line 7; (in the formula) the "$R_2'$" should read -- $R'_2$ --
Column 6, line 23; (in the formula) the "$R_2'$" should read -- $R'_2$ --
Column 6, line 40; (in the formula) the "$R_2'$" should read -- $R'_2$ --
Column 6, line 57; (in the formula) the "$R_2'$" should read -- $R'_2$ --
Column 7, line 4; (in the formula) the "$R_2'$" should read -- $R'_2$ --
Column 7, line 17; (in the formula) the "$R_2'$" should read -- $R'_2$ --
Column 7, line 39; (in the formula) the "$R_2'$" should read -- $R'_2$ --
Column 7, line 55; (in the formula) the "$R_2'$" should read -- $R'_2$ --
Column 8, line 5; (in the formula) the "$R_2'$" should read -- $R'_2$ --
Column 8, line 22; (in the formula) the "$R_2'$" should read -- $R'_2$ --
Column 8, line 48; (in the formula) the "$R_2'$" should read -- $R'_2$ --
Column 8, line 57; (in the formula) the "$R_2'$" should read -- $R'_2$ --
Column 9, line 5; (in the formula) the "$R_2'$" should read -- $R'_2$ --
Column 9, line 12; (in the formula) the "$R_2'$" should read -- $R'_2$ --
Column 9, line 22; delete the "$C_1-$
Column 9, line 23; insert at the beginning of the line "($C_1-$" to read -- ($C_1-C_6$) --

UNITED STATES PATENT AND TRADEMARK OFFICE
CERTIFICATE OF CORRECTION

PATENT NO. : 5,387,591

DATED : February 7, 1995

INVENTOR(S) : Gilbert Lavielle, Thierry Dubuffet, Olivier Muller, Michel Laubie, Tony Verbeuren It is certified that error appears in the above-indentified patent and that said Letters Patent is hereby corrected as shown below:

Column 9, line 30; (in the formula) "$R_2'$" should read -- $R'_2$ --

Column 9, line 45; (in the formula) "$R_2'$" should read -- $R'_2$ --

Column 13, line 32; "($CDC_{13}$/TMS):" should read -- $CDCl_3$/TMS): --

Column 16, line 40; delete the word "gel," and then insert the word "gel," between the words "silica" and "using"

Column 30, line 41; insert a comma "," after the word "alkoxy"

Column 31, line 10; delete the word "the" and insert the word "those"

Column 31, line 12; insert a comma "," after the word "epimers" (Prel.

Column 31, line 14; delete the word "the" and insert the word "those"

UNITED STATES PATENT AND TRADEMARK OFFICE
CERTIFICATE OF CORRECTION

PATENT NO. : 5,387,591

DATED : February 7, 1995

INVENTOR(S) : Gilbert Lavielle, Thierry Dubuffet, Olivier Muller, Michel Laubie, Tony Verbeuren It is certified that error appears in the above-indentified patent and that said Letters Patent is hereby corrected as shown below:

Column 32, line 1; Change "selected from which is" to -- which is selected from --
Column 32, line 4; insert a hyphen "-" after the word "pharmaceutically"
Column 32, line 5; Change "selected from which is" to -- which is selected from --
Column 32, line 8; insert a hyphen "-" after the word "pharmaceutically"
Column 32, line 9; Change "selected from which is" to -- which is selected from --

Signed and Sealed this

Thirteenth Day of June, 1995

BRUCE LEHMAN

Attest:

Attesting Officer

Commissioner of Patents and Trademarks